United States Patent [19]
Maeda et al.

[11] Patent Number: 5,665,518
[45] Date of Patent: Sep. 9, 1997

[54] PHOTORESIST AND MONOMER AND POLYMER FOR COMPOSING THE PHOTORESIST

[75] Inventors: Katsumi Maeda; Kaichiro Nakano; Takeshi Ohfuji; Etsuo Hasegawa, all of Tokyo, Japan

[73] Assignee: NEC Corporation, Tokyo, Japan

[21] Appl. No.: 588,607

[22] Filed: Jan. 19, 1996

[30] Foreign Application Priority Data

Jan. 26, 1995 [JP] Japan .................... 7-011043
Aug. 9, 1995 [JP] Japan .................... 7-203150

[51] Int. Cl.$^6$ .................. G03F 7/039; C07C 69/54; C07D 309/12; C07D 307/20
[52] U.S. Cl. .................. 430/270.1; 526/282; 525/312; 525/329.5; 549/420; 560/220
[58] Field of Search .................. 430/270.1; 526/282; 525/312, 329.5; 549/420; 560/220

[56] References Cited

U.S. PATENT DOCUMENTS

| | | | |
|---|---|---|---|
| 4,332,964 | 6/1982 | Bellmann et al. | 560/220 X |
| 4,835,027 | 5/1989 | Sudo et al. | 430/285.1 X |
| 4,948,700 | 8/1990 | Maeda et al. | 430/280.1 |
| 5,230,984 | 7/1993 | Tachiki et al. | 430/270.1 |
| 5,314,785 | 5/1994 | Vogel et al. | 430/270.1 |

FOREIGN PATENT DOCUMENTS

| | | | |
|---|---|---|---|
| 64-1759A | 1/1989 | Japan | 526/282 |
| 2-27660 | 6/1990 | Japan | |
| 5-134416 | 5/1993 | Japan | |
| 5-265212 | 10/1993 | Japan | |
| 6-167810A | 6/1994 | Japan | 430/270.1 |

OTHER PUBLICATIONS

"Applications of Photoinitiators to the Design of Resists for Semiconductor Manufacturing," H. Ito et al., American Chemical Society Symposium, vol. 242, pp. 11–23, 1984.

"ArF Excimer Laser Lithography (3),", M. Sasago et al., 36th Applied Physics Institution Conference Manuscripts, 1p–K–4, p. 562, 1989 (Japanese–no translation).

"Lithographic Characteristics of Alicyclic Polymer Based ArF Single Layer Resists," M. Takahashi et al., Journal of Photopolymer Science and Technology, vol. 7, No. 1, pp. 31–39, 1984.

(List continued on next page.)

*Primary Examiner*—Cynthia Hamilton
*Attorney, Agent, or Firm*—Young & Thompson

[57] ABSTRACT

The present invention provides a vinylmonomer represented with the following general formula (I):

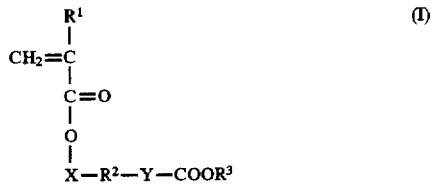

wherein $R^1$ represents a hydrogen atom or a methyl group, $R^2$ represents a dihydric, bridged cyclic hydrocarbon group having a carbon number in the range of 7 to 13 both inclusive, $R^3$ represents a group to be decomposed by acid or a hydrogen atom, X represents an alkylene group or a coupling group composed of an oxygen-carbon bond, and Y represents an alkylene group or a coupling group composed of a carbon-carbon bond. A photoresist obtained by polymerizing a monomer in accordance with the invention has a high transparency to FUV having a wavelength of at greatest 220 nm, high sensitivity and resolution to FUV, and a high dry etching resistance, and hence is suitable for exposure light such as FUV having a wavelength of at greatest 220 nm and, in particular, ArF excimer laser. The photoresist makes it possible to carry out fine patterning required for the fabrication of a semiconductor element.

3 Claims, 1 Drawing Sheet

OTHER PUBLICATIONS

"Resolution and Etch Resistance of a Family of 193 nm Positive Resists," R. D. Allen et al., Journal of Photopolymer Science and Technology, vol. 8, No. 4, pp. 623–636, 1995.

"Challenges in Excimer Laser Lithography for 256M DRAM and Beyond," M. Endo et al., IEDM Tech. Digest, pp. 45–48, 1992.

"Single–Layer Chemically Amplified Photoresists for 193–nm Lithography," G. M. Wallraff et al., J. Vac. Sci. Technol. B 11(6), pp. 2783–2788, Nov./Dec. 1993.

"Single Layer Resists with Enhanced Etch Resistance for 193 nm Lithography," R. D. Allen et al., Journal of Photopolymer Science and Technology, vol. 7, No. 3, pp. 507–516, 1994.

"Highly Transparent Chemically Amplified ArF Excimer Laser Resists by Absorption Band Shift for 193 nm Wavelength," T. Naito et al., Jpn. J. Appl. Phys., vol. 33, pp. 7028–7032, Dec. 1994.

"Alicyclic Polymer for ArF and KrF Excimer Resist Based on Chemical Amplification," S. Takechi et al., Journal of Photopolymer Science and Technology, vol. 5, No. 3, pp. 439–445, 1992.

"A New Prepartaion of Triarylsulfonium and –selenomium Salts via the Copper(II)–Catalyzed Arylation of Sulfides and Selenides with Diaryliodonium Salts," J. V. Crivello et al., J. Org. Chem., vol. 43, No. 15, pp. 3055–3058, 1978.

"Development of a Chemically Amplified Positive (CAMP) Resist Material for Single Layer Deep–UV Lithography," O. Nalamasu et al., SPIE, vol. 1262, pp. 32–48, 1990.

"Chemical Amplication Positive Resist Systems Using Novel Sulfonates as Acid Generators," T. Ueno et al., Proceedings of PME '89, pp. 413–424, 1990.

PHOTORESIST AND MONOMER AND POLYMER FOR COMPOSING THE PHOTORESIST

BACKGROUND OF THE INVENTION

1. Field of the Invention

The present invention relates to photoresist material suitable for lithography used in the fabrication of a semiconductor where far ultraviolet radiation (FUV) having a wavelength equal to or smaller than 220 nm is to be used as an exposure light, and also relates to monomer and polymer of which the photoresist is to be composed.

2. Description of the Related Art

In a field of manufacturing various electronic devices such as a semiconductor device, an electric device is now required to be more highly densified and integrated. Thus, an improved lithography technique for forming a more minute pattern on a substrate is required for satisfying such a requirement.

As one of methods for forming a more minute pattern is known a method in which an exposure light having a shorter wavelength is used for forming a resist pattern. For instance, in a mass production of a 0.25 μm-rule 256M bits dynamic random access memory (DRAM), it is now being studied that as an exposure light source the i-line having a wavelength of 365 μm is replaced with KrF excimer laser having a shorter wavelength than that of the i-line, more specifically, having a wavelength of 248 nm. However, the fabrication of 0.2 μm-rule 1 G bits DRAM which requires a technique enabling more fine processing needs a light source having a shorter wavelength than that of KrF excimer laser to be developed. For that purpose, an ArF excimer laser having a wavelength of 193 nm now attracts attention as a light source to be used in photolithography.

In addition, a resist to be used for minute processing is required to have a high sensitivity as well as a high resolution in response to a design rule getting smaller and smaller. This is because it is necessary to improve cost performance since an excimer laser to be used as a light source is expensive. As one of methods of enhancing a sensitivity of resist is known a chemically amplified resist which utilizes a photo add generator as a sensitizer. For typical instance, Japanese Patent Application No. 2-27660 has suggested a resist comprising a combination of triphenylsulfonium-.hexafluoroarsenate and poly (p-tert-butoxycarbonyloxy-α-methylstyrene). There are many reports about a chemically amplified resist for use with a KrF excimer laser, for instance, one of which is American Chemical Society Symposium Series, 1984, Vol. 242, pages 11–23, reported by Hiroshi Ito and C. Grantwilson. A chemically amplified resist is characterized by the steps of generating proton acid by exposing a sensitizer or a photo acid generator to a light, transferring the thus generated proton acid through a resist solid phase by means of post-exposure heat treatment to thereby amplify chemical reaction of the resist resin up to hundreds of to thousands of times due to the proton acid in a way like catalytic action. Thus, a quite higher sensitivity can be attained relative to prior resist which has an optical reaction efficiency, which is defined as a reaction per a photon, of smaller than one (1).

Presently, most of newly developed resist is a chemically amplified resist, and hence a chemical amplification system has to be adopted in development of a high sensitive material in response to a shorter wavelength of an exposure light source.

In a lithography technique in which there is to be used an excimer laser such as ArF excimer laser, having a wavelength shorter than 220 nm as an exposure light, a resist for forming a minute pattern is required to have new characteristics which prior resist did not have.

The above mentioned new characteristics with respect to a sensitizer or a photo acid generator are (a) high transparency to exposure lights having a wavelength equal to or smaller than 220 nm, and (b) high reaction efficiency or high photo acid generation ability to the same exposure lights.

In order to satisfy those requirements, the inventors had already developed novel photo acid generators and suggested in Japanese Unexamined Patent Publications Nos. 7-25846 and 7-28237 and Japanese Patent Application No. 6-162244. It should be noted that these publications and application are listed herein merely for better understanding of the present invention, and that the inventors do not admit these publications and application as prior art.

The above mentioned new characteristics with respect to constituents of a resin are (a) high transparency to exposure lights having a wavelength equal to or smaller than 220 nm, and (b) etching-resistance.

In a conventional lithography in which there is used g-line having a wavelength of 436 nm, i-line having a wavelength of 365 nm or KrF excimer laser having a wavelength of 248 nm, a resin constituent of photoresist material is selected from resins which include aromatic rings in a unit structure, such as novolac resin and poly (p-vinylphenol). The dry etching resistance of such aromatic rings gives a dry etching resistance to the above mentioned resin.

However, the aromatic rings quite intensively absorbs lights having a wavelength equal to or shorter than 220 nm, and hence the above mentioned conventional resins cannot be applied to a photolithography which uses an exposure light having a wavelength equal to or shorter than 220 nm. Specifically, most of exposure lights is absorbed at a surface of a resist, and accordingly cannot reach a substrate with the result that a minute resist pattern cannot be formed. Such a fact has been reported, for instance, in "ArF excimer laser lithography (3)—Evaluation of Resist—", the 36th Applied Physics Institution Conference Manuscripts, 1989, 1p-K-4 by Sasago et al. Thus, there is an eager demand of resin materials which do not include aromatic rings, but have a dry etching resistance.

For instance, as a polymer having a transparency to ArF excimer laser having a wavelength of 193 nm and further having a dry-etching resistance, there has been reported a copolymer having adamantylmethacrylate units which are alicyclic polymer in Journal of Photopolymer Science and Technology, 1994, Vol. 7, No. 1, pp 31–40, by Takahashi et al., and Japanese Unexamined Patent Publication No. 5-265212. For another instance, a copolymer having isobornylmethacrylate units has been suggested in Journal of Photopolymer Science and Technology, 1995, Vol. 8, No. 4, pp 623–636, by R. D. Allen et al.

However, the former resin does not have a residue in a residue including therein adamantane and having a dry etching characteristic or in a residue including therein isobornyl, which resin is capable of indicating a difference in solubility between pre-exposure anal post-exposure. In addition, these alicyclic alkyl groups do not include a residue such as a carboxyl group which has solubility to alkaline aqueous solution and a characteristic of adhesion to a substrate. Thus, a polymer composed only of a monomer including alicyclic alkyl groups exhibits high hydrophobic property, and hence also exhibit a weak adhesion to a silicon substrate. Hence, it was quite difficult to form uniform coverage with high reproducibility. In addition, since the above mentioned polymer does not have a residue which can exhibit a difference in solubility between pre-exposure and post-exposure, it is not possible to form a resist pattern by exposure to light. Accordingly, the former resin can be used as a resin constituent of a resist only when they are copolymerized with a comonomer capable of indicating a difference in solubility, such as 3-oxocyclohexylmethacrylate and t-butylmethacrylate, or with a comonomer having an adhesion property to a substrate such as methacrylic acid. Furthermore, since a content ratio of comonomer is required to be approximately 50 mol % and a comonomer unit such as tert-butylmethacrylate and methacrylic acid has quite low dry etching resistance, the dry etching resistance effect caused by adamantane or isobornane skeleton is remarkably deteriorated with the result that the above mentioned resins are not practical as dry etching resistant resin.

Thus, there is demanded a novel material of which photoresist is to be composed, which material has a high transparency to a light having a wavelength equal to or shorter than 220 nm, a high dry etching resistance, a functional group capable of indicating a difference in solubility between pre-exposure and post-exposure, ability of being developed with alkaline aqueous solution subsequently to exposure, and an enhanced adhesion to a substrate.

Other resists than the above mentioned ones and various lithography techniques have been reported as follows.

In "Challenges in Excimer Laser Lithography for 256M DRAM and beyond", International Electron Devices Meeting (IEDM) Technology Digest 1992, pp 45–48, by M. Endo et al., a new chemically amplified positive resist and off-axis illumination technique of KrF excimer laser lithography has been suggested. According to this article, the suggested resist and lithography were successfully applied to the fabrication of 0.25 μm-rule 256M DRAM.

In "Single-layer chemically amplified photoresists for 193-nm lithography", J. Vac. Sci. Technol. B 11(6), November/December 1993, pp 2783–2788, by G. M. Wallraft, there has been suggested a 193 nm single layer resist system based on methacrylate terpolymers. A terpolymer system based on tert-butylmethacrylate, methyl methacrylate and methacrylic acid developed for laser direct imaging applications has been adopted for high resolution imaging by modifying the terpolymer composition and by optimizing the photoacid generator loading.

In "Single Layer Resists with Enhanced Etch Resistance for 193 nm Lithography", Journal of Photopolymer Science and Technology, Vol. 7, No. 3, 1994, pp 507–516, by Robert D. Allen et al., there has been suggested a positive chemically amplified (CA) resist for 193 nm lithography. This paper discusses structure/property relationships of methacrylate polymers with increased etch resistance over the first generation resist.

In "Highly Transparent Chemically Amplified ArF Excimer Laser Resists by Absorption Band Shift for 193 nm Wavelength", Jpn. J. Appl. Phys. Vol. 33 (1994), pp 7028–7032, Part 1, No. 12B, December 1994, by Takuya NAITO et al., naphthalene-containing chemically amplified resists for ArF excimer laser have been proposed, based on the concept of the absorption band shift by conjugation extension. According to the article, the sensitivity of the proposed resist is 150 mJ/cm$^2$, which is 20 times greater than that of poly (methylmethacrylate) (PMMA).

In "Alicyclic Polymer for ArF and KrF Excimer Resist Based on Chemical Amplification", Journal of Photopolymer Science and Technology, Vol. 5, No. 3 (1992), pp 439–446, by Satoshi Takechi et al., it has been reported that the polymers having an alicyclic hydrocarbon show dry-etch resistance comparable to Novolac resists. Based on this discovery, a new chemical amplification resist has been proposed for ArF and KrF excimer lithography. The resist comprises the copolymer of adamantylmethacrylate and tert-butylmethacrylate with triphenylsulfonium hexafluoroantimonate as a photo acid generator. According to the report, the use of the proposed resist enables 0.40 micron lines and spaces using KrF excimer stepper.

SUMMARY OF THE INVENTION

In view of the shortcomings of prior photoresist, it is an object of the present invention to provide photoresist material to be used in lithography in which there is used an exposure light having a wavelength equal to or smaller than 220 nm, in particular, greater than 180 nm but smaller than 220 nm, which photoresist material has a sufficient transparency, dry-etching resistance, high resolution, and high solubility to a developing solution.

It is another object of the present invention to provide monomer and polymer suitable for synthesis of the above mentioned photoresist material.

The present invention provides a vinylmonomer represented with the following general formula (I):

wherein $R^1$ represents one of a hydrogen atom and a methyl group, $R^2$ represents a dihydric, bridged cyclic hydrocarbon group having a carbon number in the range of 7 to 13 both inclusive, $R^3$ represents one of a group to be decomposed by acid and a hydrogen atom, X represents one of an alkylene group and a coupling group composed of an oxygen-carbon bond, and Y represents one of an alkylene group and a coupling group composed of a carbon-carbon bond.

The dihydric, bridged cyclic hydrocarbon group represented with $R^2$ includes, for instance, a tricyclo[5.2.1.0$^{2,6}$] decanediyl group, an adamantanediyl group, a norbornanediyl group, a methylnorbornanediyl group, an isobornanediyl group, a tetracyclo[4.4.0.1$^{2,5}$.1$^{7,10}$] dodecanediyl group, and a methyltetracyclo[4.4.0.1$^{2,5}$.1$^{7,10}$] dodecanediyl group, as shown in Table 1. However, the dihydric, bridged cyclic hydrocarbon group $R^2$ is not to be limited to those.

The group represented with $R^3$ includes, for instance, a tert-butyl group, a tetrahydropyran-2-yl group, a tetrahydrofuran-2-yl group, a 4-methoxytetrahydrofuran-4-yl group, a 1-ethoxyethyl group, a 1-butoxyethyl group, a 1-propoxyethyl group, and a 3-oxocyclohexyl group. However, the group $R^3$ is not to be limited to the above listed groups.

The alkylene group represented with X or Y is selected from, for instance, —CH$_2$— and —CH$_2$CH$_2$—, but is not to be limited to those.

TABLE 1

| R², R⁵, R⁷ | Chemical Structure of Group |
|---|---|
| Tricyclo [5. 2. 1. 0²,⁶] decanediyl Group |  or  |
| Adamantanediyl Group |  |
| Norbornanediyl Group |  |
| Methylnorbornanediyl Group |  |
| Isobornanediyl Group |  |
| Tetracyclo [4. 4. 0. 1²,⁵. 1⁷,¹⁰] dodecanediyl Group |  |
| Methyltetracyclo [4. 4. 0. 1²,⁵. 1⁷,¹⁰] dodecanediyl Group |  |

The present invention further provides a polymer composed by polymerizing vinylmonomer with each other, the vinylmonomer being represented with the above mentioned general formula (I).

The present invention still further provides a polymer composed by copolymerizing vinylmonomer represented with the above mentioned general formula (I) with polymeric compounds.

An example of these polymers is represented with the following general formula (II):

$$\begin{array}{ccc}
R^4 & R^6 & R^9 \\
| & | & | \\
\text{+CH}_2\text{—C+} & \text{+CH}_2\text{—C+} & \text{+CH}_2\text{—C+} \\
| & | & | \\
C=O & C=O & C=O \\
| & | & | \\
O & O & O \\
| & | & | \\
A\text{—}R^5\text{—}B\text{—COOH} & D\text{—}R^7\text{—}E\text{—COOR}^8 & R^{10}
\end{array} \quad (II)$$

wherein each of $R^4$, $R^6$ and $R^9$ represents a hydrogen atom or a methyl group, each of $R^5$ and $R^7$ represents a dihydric, bridged cyclic hydrocarbon group having a carbon number in the range of 7 to 13 both inclusive, $R^8$ represents a group to be decomposed by acid, $R^{10}$ represents a hydrogen atom or a hydrocarbon group having a carbon number in the range of 1 to 10 both inclusive, k and m are variables varying in the range of 0 to 1.0, n is a variable varying in the range of 0 to 0.9, k+m+n=1.0, each of A and D represents an alkylene group or a coupling group composed of an oxygen-carbon bond, and each of B and E represents an alkylene group or a coupling group composed of an carbon-carbon bond, and wherein the polymer has a weight average molecular weight in the range of 1,000 to 500,000 both inclusive.

The dihydric, bridged cyclic hydrocarbon group represented with $R^5$ or $R^7$ is selected from, for instance, a tricyclo[5.2.1.0²,⁶]decanediyl group, an adamantanediyl group, a norbornanediyl group, a methylnorbornanediyl group, an isobornanediyl group, a tetracyclo[4.4.0.1²,⁵.1⁷,¹⁰]dodecanediyl group, and a methyltetracyclo[4.4.0.1²,⁵.1⁷,¹⁰]dodecanediyl group, as shown in Table 1. However, it should be noted that the dihydric, bridged cyclic hydrocarbon group $R^5$ or $R^7$ is not to be limited to the above mentioned groups.

The group represented with $R^8$ is selected from, for instance, a tert-butyl group, a tetrahydropyran-2-yl group, a tetrahydrofuran-2-yl group, a 4-methoxytetrahydrofuran-4-yl group, a 1-ethoxyethyl group, a 1-butoxyethyl group, a 1-propoxyethyl group, and a 3-oxocyclohexyl group. It should be noted that the group $R^8$ is not to be limited to the above mentioned groups.

The hydrocarbon group represented with $R^{10}$ is selected from, for instance, a methyl group, an ethyl group, an n-propyl group, an isopropyl group, an n-butyl group, an isobutyl group, a tert-butyl group, a cyclohexyl group, a dimethylcyclohexyl group, a tricyclo[5.2.1.0²,⁶]decanyl group, a norbonyl group, an adamantyl group, and an isobornyl group. The hydrocarbon group represented with $R^{10}$ is preferably selected from a bridged, cyclic hydrocarbon group such as a tricyclo[5.2.1.0²,⁶]decanyl group, a norbonyl group, an adamantyl group, and an isobornyl group. The hydrocarbon group $R^{10}$ is not to be limited to the above mentioned groups.

The alkylene group represented with A, D, B or E is selected from, for instance, —CH₂— and —CH₂CH₂—, but is not to be limited to those.

Among vinyl monomers represented with the general formula (I), a vinylmonomer wherein $R^1$ is a methyl group, $R^2$ is a tricyclo[5.2.1.0²,⁶]decane-4,8-diyl group, $R^3$ is a hydrogen atom, X is —CH₂—, and Y is a coupling group composed of carbon-carbon bonds, is synthesized as follows, for instance. First, into tricyclo[5.2.1.0²,⁶]decane-4,8-dimethanol present in dry tetrahydrofuran solvent is dropped methacryloyl chloride having the same mol as that of tricyclo [5.2.1.0²,⁶]decane-4,8-dimethanol while being cooled with ice under the presence of base such as pyridine having the same mol as that of tricyclo[5.2.1.0²,⁶]decane-4,8-dimethanol. Then, the mixture is stood for ten hours for reaction at room temperature (RT) to thereby synthesize monoacrylate of tricyclo [5.2.1.0²,⁶]decane-4,8-dimethanol. Then, the thus synthesized compound is made to react with dichromate pyridinium, which has three and a half greater mols than the compound, for ten hours at RT in N,N-dimethylformamide solvent. Thus, the aimed vinylmonomer is obtained.

Among vinylmonomers represented with the general formula (I), a vinylmonomer wherein $R^1$ is a methyl group, $R^2$ is a tricyclo[5.2.1.0²,⁶]decane-4,8-diyl group, $R^3$ is a tetrahydropyran-2-yl group, X is —CH₂—, and Y is a coupling group composed of carbon-carbon bonds, is synthesized as follows, for instance. The vinylmonomer synthesized in accordance with the formerly described process, wherein $R^1$ is a methyl group, $R^2$ is a tricyclo[5.2.1.0²,⁶]decane-4,8-diyl group, $R^3$ is a hydrogen atom, X is —$CH_2$—, and Y is a coupling group composed of carbon-carbon bonds, is made to react with 3,4-dihydro-2H-pyran, while being cooled with ice, under the presence of methylene chloride solvent and also of p-toluenesulfonic acid having an amount sufficient as a catalyst. Thus, the aimed vinylmonomer can be obtained.

A homopolymer of vinylmonomer represented with the general formula (I), and a copolymer synthesized by copolymerizing vinylmonomer represented with the general formula (I) with another polymeric compound can be obtained by means of conventional polymerization processes such as radical polymerization and ion polymerization. For instance, in one of such processes, a suitable radical polymerization initiator (for instance, a mixture ratio in mol between azobisisobutyronitrile and monomer/initiator is in the range of 8 to 200) is added into the above mentioned polymers in dry tetrahydrofuran solution under inert gas atmosphere such as argon (Ar) and nitrogen (N2), and then the mixture is stirred, while being heated, for 5 to 12 hours at temperature in the range of 50 to 70 degrees centigrade.

The polymer in accordance with the present invention has a weight average molecular weight in the range of 1,000 to 500,000 both inclusive, and preferably in the range of 5,000 to 200,000 both inclusive.

The copolymer may have a desired copolymerization ratio by varying a mixture ratio of monomers and other polymerization conditions.

The inventors have confirmed that a 1.0 μm thick film composed of either a homopolymer of vinylmonomer represented with the general formula (I) or a polymer composed by copolymerizing vinylmonomer represented with the general formula (I) with other polymeric compounds has the transmissivity ranging from 65% to 80% both inclusive against ArF excimer laser (193 nm), and that such a thin film is quite practical. In addition, the inventors have further confirmed that a deposited film composed of the polymer in accordance with the invention has high adhesion to a silicon substrate, and hence it is possible to carry out uniform deposition with high reproducibility. The inventors have still further confirmed that the polymer in accordance with the invention has superior dry-etch resistance.

The photoresist in accordance with the invention basically includes the above mentioned polymer, a photo acid generator and a solvent.

In general, a photo acid generator generates an acid when exposed to light. A photo acid generator to be used for the invention is one that generates an acid when exposed to light which preferably has a wavelength equal to or less than 300 nm, more preferably 220 nm. In the present invention, any photo acid generator may be used if a mixture of the earlier mentioned polymer in accordance with the invention and the photo acid generator is sufficiently soluble in an organic solvent, and further if it is possible to form a uniform deposition layer from the solution by means of a layer forming process such as spin coating process. One or more photo acid generators may be mixed for use with the invention. In an alternative, a photo acid generator may be used in combination with photosensitizer.

Photo acid generators usable for reducing the present invention into practice may be selected, for instance, from any one of (a) triphenylsulfonium salt derivatives proposed in Journal of the Organic Chemistry, 1978, Vol. 43, No. 15, pp 3055–3058, by J. V. Crivello et al., (b) onium salts such as sulfonium salt, iodonium salt, phosphonium salt, diazonium salt and ammonium salt, (c) 2,6-dinitrobenzyl ester proposed in SPIE Proceedings, 1990, Vol. 1262, pp 32, by O. Nalamasu et al., (d), 1,2,3-tri (methanesulfonyloxy) benzene proposed in Proceedings of PME '89, 1990, pp 413–424, by Takumi Ueno et al., published through Kodansha, (e) sulfonium salt disclosed in Japanese Unexamined Patent Publications Nos. 7-25846 and 7-28237 and Japanese Patent Application No. 6-162244, and (f) sulfosuccinimide represented with the general formula (IV) disclosed in Japanese Unexamined Patent Publication No. 5-134416. However, it should be noted that a photo acid generator to be used for the invention is not to be limited to the above mentioned ones (a) to (f).

In the general formula (III), each of $R^{11}$ and $R^{12}$ indicates a straight-chain, branch-type or cyclic alkyl group, and $R^{13}$ indicates one of straight-chain, branch-type and cyclic alkyl groups, a 2-oxocyclicalkyl group, a 2-oxostraight-chain alkyl group or a 2-oxobranch-type alkyl group, and Z- represents a twin ion such as $BF_4-$, $AsF_6-$, $SbF_6-$, $PF_6-$, $CF_3COO-$, $ClO_4-$, $CF_3SO_3-$, alkylsulfonate and arylsulfonate.

In the general formula (IV), each of $R^{14}$ and $R^{15}$ indicates hydrogen, a straight-chain, branch-type or cyclic alkyl group, and $R^{16}$ indicates one of a straight-chain alkyl group, a branch type alkyl group, a cyclic alkyl group, and a haloalkyl group typified by perfluoroalkyl such as trifluoromethyl.

When an exposure light having a wavelength equal to or shorter than 220 nm is to be used, it is preferable to select a photo acid generator indicated by the general formula (III) or (IV) for enhancing light transmissivity of photoresist material. A photo acid generator such as triphenylsulfonium trifluoromethanesulfonate (hereinafter, referred to as TPS) presently, widely used for KrF excimer laser lithography has a quite strong light-absorbing property in the range of far ultraviolet radiation (FUV) having a wavelength equal to or shorter than 220 nm, and hence it is required to limit an amount thereof if it is to be used as a photo acid generator in the present invention. Now comparing a transmissivity at a wavelength of 193.4 nm which is a main wavelength of ArF excimer laser beam, a transmissivity of a deposition film (1 μm thick) composed of polymethylmethacrylate containing TPS at 1.5 weight part on the basis of a total weight of the film was approximately 50%, and a transmissivity of a film (1 μm thick) composed of the same containing TPS at 5.5 weight part was approximately 6%. On the other hand, a transmissivity of a polymethylmethacrylate deposition film containing therein, for instance, cyclohexylmethyl(2-oxocyclohexyl)sulfoniumtrifluoromethanesulfonate, which is one of sulfonium salt derivatives represented with the general formula (III), at 5 weight part was 71%, and at 30 weight part was 55%, both of which are higher than the formerly mentioned transmissivity.

Thus, any of the photo acid generators represented with the general formulas (III) and (IV) absorbs quite little amount of light in the band of FUV having a wavelength ranging from 185.5 nm to 220 nm, and accordingly it is obvious that they are preferable for a constituent of a resist to be used for ArF excimer laser lithography in terms of transparency to an exposure light. Specifically, a photo acid generator to be used in the invention may be selected from any one of (a) 2-oxocyclohexylmethyl(2norbornyl) sulfoniumtrifluoromethanesulfonate, (b) cyclohexylmethyl (2-oxocyclohexyl)sulfoniumtrifluoromethanesulfonate, (c) dicyclohexyl(2-oxocyclohexyl)sulfoniumtrifluoromethanesufonate, (d) 2-cyclohexylsulfonylcyclohexanone, (e) dimethyl(2-oxocyclohexyl)sulfoniumtrifluoromethanesulfonate, (f) triphenylsulfoniumtrifluoromethanesulfonate, (g) diphenyliodoniumtrifluoromethanesulfonate, and (h) N-hydroxysuccinimidetrifluoromethanesulfonate. However, it should be noted that a photo acid generator to be used in the invention is not to be limited to those, and any other photo acid generator may be selected.

A single kind of or a plurality of kinds of photo acid generator(s) may be used in the photoresist in accordance with the invention. The photo acid generator is contained by weight part preferably in the range from 0.2 to 30 both inclusive, and more preferably in the range from 1 to 15 both inclusive, provided that all constituents containing the photo acid generator constitute 100 weight parts. If a content rate of the photo acid generator would be lower than 0.5 weight part, the photoresist could have only quite a small sensitivity, and hence the formation of a pattern becomes difficult. On the other hand, if a content rate of the photo acid generator would be higher than 30 weight part, it would be difficult to form a uniform deposition layer, and further there would arise a problem that scum tends to be generated after development of a pattern. A content rate of the polymer is preferably in the range from 70 to 99. 8 weight part, and more preferably in the range from 85 to 99 weight part on the basis of the 100 weight part of all constituents including the polymer itself.

Any organic solvent may be used in the invention, if a constituent composed of polymer and photo acid generator would be sufficiently soluble in a solvent, and if it would be possible to form a uniform deposition layer from the solution by means of a method such as spin coating process. A single kind of solvent or a plurality of kinds of solvents in combination may be used.

Specifically, a solvent to be used in the invention is selected from any one of n-propyl alcohol, isopropyl alcohol, n-butyl alcohol, tert-butyl alcohol, methylcellosolve acetate, ethylcellosolve acetate, propyleneglycol monoethylether acetate, methyl lactate, ethyl lactate, 2-methoxybutyl acetate, 2ethoxyethyl acetate, pyrubic acid methyl, pyrubic acid ethyl, 3-methoxypropionatemethyl, 3-methoxypropionateethyl, N-methyl-2-pyrrolidinone, cyclohexanone, cyclopentanone, cyclohexanol, methylethylketone, 1,4-dioxan, ethyleneglycolmonomethylether, ethyleneglycolmonomethylether acetate, ethyleneglycolmonoethylether, ethyleneglycolmonoisopropylether, diethyleneglycolmonomethylether, and diethyleneglycoldimethylether. It should be noted that a solvent to be used in the invention is not to be limited to the above mentioned ones, other solvents may be selected.

As having been explained, basic constituents of the photoresist in accordance with the invention are the above mentioned photo acid generator, polymer and solvent. However, the photoresist may include other constituents such as agent for preventing dissolution, surfactant, pigment, stabilizer, reagent for enhancing application property, and dye.

The present invention yet further provides a method of patterning including the steps of (a) applying the photoresist on a substrate, (b) prebaking the substrate having the photoresist applied thereon, (c) applying selective exposure to the photoresist by using far ultraviolet radiation having a wavelength of at greatest 220 nanometers, (d) baking the substrate having the photoresist applied thereon, and (e) developing the substrate to thereby form a resist pattern.

The polymer to be used in this method may be selected from any one of following (a) to (c):

(a) a polymer composed by polymerizing vinylmonomer with each other, the vinylmonomer represented with the above mentioned general formula (I);

(b) a polymer composed by copolymerizing vinylmonomer represented with the general formula (I) with other polymeric compounds; and (c) a polymer represented with the general formula (II).

Thus, the present invention provides novel photoresist which has (a) high transparency to light having a wavelength equal to or smaller than 220 nm, (b) high dry-etch resistance, (c) a functional group capable of indicating a difference in solubility between pre-exposure and post-exposure, and (d) enhanced adhesion to a substrate. The photoresist in accordance with the invention enables to fabricate more fine patterns by using the photoresist in combination with lithography technique in which light having a wavelength equal to or smaller than 220 nm is to be used for exposure.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Preferred embodiments in accordance with the present invention will be explained hereinbelow.
[Embodiment 1]

Synthesis of vinylmonomer represented with the general formula (I) wherein $R^1$ indicates a methyl group, $R^2$ indicates a tricyclo[5.2.1.0$^{2,6}$]decane-4, 8-diyl group, $R^3$ indicates a hydrogen atom, X indicates —CH$_2$—, and Y indicates a coupling group composed of carbon-carbon bonds.

Followings were put into 500 ml flask having four inlets and equipped with a calcium chloride (CaCl$_2$) drying tube, an isotactic dropping funnel and a thermometer:

(a) 50 grams (0.25 mol) of tricyclo[5.2.1.0$^{2,6}$]decane-4, 8-dimethanol commercially available from Aldrich Chemical Company, Inc. (U.S.A.) with the lot number B4,590-9;

(b) 25.76 grams (0.25 mol) of dry pyridine; and (c) 300 ml of dry tetrahydrofuran.

The mixture was stirred so that it was uniform solution, and then cooled in ice bath. While the solution was being stirred hard with a teflon bar, into the solution was slowly dropped through a dropping funnel a solution of 100 ml of dry tetrahydrofuran into which 26.53 grams (0.25 mol) of methacryloyl chloride, commercially available from Tokyo Kasei K.K., had been dissolved. After the dropping was completed, the resultant solution was stirred in ice bath for an hour, and then was stood for reaction at room temperature (RT) for ten hours. After the precipitate was filtered away from the solution, the solvent was removed out of the filtrate under reduced pressure. Then, the residue was dissolved in 500 ml of methylene chloride. Then, the solution in which the residue was dissolved was disposed with 0.5N HCl, saturated salt aqueous solution, 3% sodium bicarbonate aqueous solution and again saturated salt aqueous solution in this order. The resultant methylene chloride layer was dehydrated with magnesium sulfate, and then was filtered. The residue which was obtained by removing the solvent by means of an evaporator was refined through a silica gel column to thereby obtain 29.6 grams of tricyclo[5.2.1.0$^{2,6}$] decane-4,8-dimethanolmonomethacrylate in the form of viscous liquid. The yield was 44%.

Then, followings were put into 100 ml flask having four inlets and equipped with a calcium chloride (CaCl$_2$) drying tube, an isotactic dropping funnel and a thermometer:

(a) 24.9 grams (66.2 mmol) of prydinium dichromate; and (b) 40 ml of N,N-dimethylformamide.

The mixture was stirred so that it was uniform solution. Then, into the solution was dropped 10 ml of N,N-dimethylformamide in which 5 grams (18.9 mmol) of tricyclo[5.2.1.0$^{2,6}$]decane-4,8-dimethanolmonomethacrylate had been dissolved. After the dropping was completed, the resultant solution was stood for reaction at room temperature (RT) for ten hours. The resultant solution was diluted with 500 ml of water, and then an organic layer was extracted with diethylether. The extraction was carried out three times with 150 ml of diethylether. A resultant ether layer was dehydrated with magnesium sulfate, and then was filtered out. The residue obtained by removing the solvent by means of an evaporator was refined through a silica gel column to thereby obtain 2.12 grams of a target material represented with the general formula (V) in the form of viscous liquid. The yield was 40%.

IR was measured with an analyzer, IR-470 model available from Shimazu Seisakusho, and $^1$H-NMR was measured with an analyzer, AMX-400 model available from Bruker Instruments.

Elemental Analysis Value (Weight %) C: 69.4 (69.0) H: 8.3 (8.0)

The figures in parentheses indicate values calculated with C$_{16}$H$_{22}$O$_4$ whose MW is 278.3474.

IR(cm$^{-1}$): 2400–3350 ($v_{OH}$), 2950 ($v_{CH}$), 1696 ($v_{C=O}$), 1626 ($v_{C=C}$), 1166 ($v_{C-O}$)

$^1$H-NMR (CDCl$_3$, internal standard material: tetramethylsilane) ppm: 0.95–2.74 (m, 14H), 1.95 (s, 3H), 3.88–4.17 (m, 2H), 5.55 (d, J=1.5 Hz, 1H), 6.1 (s, 1H), 9.58–10.8 (br s, 1H)

[Embodiment 2]

Synthesis of vinylmonomer represented with the general formula (I) wherein R$^1$ indicates a hydrogen atom, R$^2$ indicates a tricyclo[5.2.1.0$^{2,6}$]decane-4,8-diyl group, R$^3$ indicates a hydrogen atom, X indicates —CH$_2$—, and Y indicates a coupling group composed of carbon-carbon bonds.

In the same way as the embodiment 1, synthesis was performed using acryloyl chloride in place of methacryloyl chloride. There was obtained a target material represented with the general formula (VI) in the form of viscous liquid. The yield was 20%.

Elemental Analysis Value (Weight %) C: 68.6 (68.2) H: 8.0 (7.6)

The figures in parentheses indicate calculation values calculated with C$_{15}$H$_{22}$O$_4$ whose MW is 264.3206.

IR(cm$^{-1}$): 2400–3350 ($v_{OH}$), 2950 ($v_{CH}$), 1700 ($v_{C=O}$), 1630 ($v_{C=C}$), 1168 ($v_{C-O}$)

$^1$H-NMR (CDCl$_3$, internal standard material: tetramethylsilane) ppm: 0.95–2.74 (m, 14H), 3.88–4.17 (m, 2H), 5.6–6.4 (m, 3H), 9.58–10.8 (br s, 1H)

[Embodiment 3]

Synthesis of vinylmonomer represented with the general formula (I) wherein R$^1$ indicates a methyl group, R$^2$ indicates a tricyclo[5.2.1.0$^{2,6}$]decane-4,8-diyl group, R$^3$ indicates a tetrahydropyran-2-yl group, X indicates —CH$_2$—, and Y indicates a coupling group composed of carbon-carbon bonds.

Followings were put into 200 ml flask having three inlets and equipped with a calcium chloride (CaCl$_2$) drying tube and a thermometer:

(a) 6 grams (0.022 mol) of the vinylmonomer having been obtained in the embodiment 1, represented with the general formula (I) wherein R$^1$ indicates a methyl group, R$^2$ indicates a tricyclo[5.2.1.0$^{2,6}$]decane-4,8-diyl group, R$^3$ indicates a hydrogen atom, X indicates —CH$_2$—, and Y indicates a coupling group composed of carbon-carbon bonds;

(b) 4.54 grams (0.054 mol) of 3,4-dihydro-2H-pyran; and (c) 80 ml of methylene chloride.

The mixture was cooled with ice. Into the mixture was added 20 mg of p-toluenesulfonic acid.H$_2$O and stirred for 30 minutes. After the reaction was completed, the mixture was diluted with 120 ml of diethylether, and then washed with 80 ml of saturated sodium bicarbonate aqueous solution, 80 ml of saturated salt water, and 150 ml of water in this order. The resultant organic layer was dehydrated with magnesium sulfate, and then filtered out. By using an evaporator, 3,4-dihydro-2H-pyran which did not react with the solvent was removed, thereby there was obtained 6.59 grams of a target material represented with the general formula (VII) in the form of viscous liquid. The yield was 84%.

Elemental Analysis Value (Weight %) C: 69.2 (69.6) H: 8.0 (8.3)

The figures in parentheses indicate calculation values calculated with C$_{21}$H$_{30}$O$_5$ whose MW is 362.465.

IR(cm$^{-1}$): 2950, 2870 ($v_{CH}$), 1716 ($v_{C=O}$), 1632 ($v_{C=C}$), 1166 ($v_{C-O}$)

$^1$H-NMR (CDCl$_3$, internal standard material: tetramethylsilane) ppm: 1.2–2.7 (m, 20H), 1.95 (s, 3H), 3.47–3.57 (m, 1H), 3.63–3.73 (m, 1H), 3.8–4.1 (m, 2H), 5.55 (s, 1H), 5.94 (s, 1H), 6.1 (s, 1H)

[Embodiment 4]

Synthesis of vinylmonomer represented with the general formula (I) wherein R$^1$ indicates a hydrogen atom, R$^2$ indicates a tricyclo[5.2.1.0$^{2,6}$]decane-4,8-diyl group, R$^3$ indicates a tetrahydrofuran-2-yl group, X indicates —CH$_2$—, and Y indicates a coupling group composed of carbon-carbon bonds.

(VIII)

In the same way as the embodiment 3, synthesis was carried out using the vinylmonomer having been obtained in the embodiment 2 in place of the vinylmonomer having been obtained in the embodiment 1, and also using 2,3-dihydrofuran in place of 3,4-dihydro-2H-pyran. The obtained target material represented with the general formula (VIII) was in the form of viscous liquid. The yield was 62%.

Elemental Analysis Value (Weight %) C: 68.3 (68.2) H: 8.1 (7.8)

The figures in parentheses indicate calculation values calculated with C$_{19}$H$_{26}$O$_5$ whose MW is 334.4114.

IR(cm$^{-1}$): 2950, 2874 ($v_{CH}$), 1718 ($v_{C=O}$), 1630 ($v_{C=C}$), 1166 ($v_{C-O-C}$)

$^1$H-NMR (CDCl$_3$, internal standard material: tetramethylsilane) ppm: 1.1–2.8 (m, 18H), 3.5–3.8 (m, 2H), 3.8–4.1 (m, 2H), 5.6–6.5 (m, 4H)

[Embodiment 5]

Synthesis of vinylmonomer represented with the general formula (I) wherein R$^1$ indicates a methyl group, R$^2$ indicates a tricyclo[5.2.1.0$^{2,6}$]decane-4,8-diyl group, R$^3$ indicates a 1-ethoxyethyl group, X indicates —CH$_2$—, and Y indicates a coupling group composed of carbon-carbon bonds.

(IX)

Followings were put into 200 ml flask having three inlets and equipped with a calcium chloride (CaCl$_2$) drying tube and a thermometer:

(a) 6 grams (0.022 mol) of the vinylmonomer having been obtained in the embodiment 1, represented with the general formula (I) wherein R$^1$ indicates a methyl group, R$^2$ indicates a tricyclo[5.2.1.0$^{2,6}$]decane-4,8-diyl group, R$^3$ indicates a hydrogen atom, X indicates —CH$_2$—, and Y indicates a coupling group composed of carbon-carbon bonds;

(b) 1.30 grams (0.022 mmol) of vinylethylether; and (c) 60 ml of methylene chloride.

The mixture was cooled with ice. Into the mixture was added 15 mg of p-toluenesulfonic acid.H$_2$O, and stirred for an hour. After the reaction was completed, the mixture was diluted with 120 ml of diethylether, and then washed with 80 ml of saturated sodium bicarbonate aqueous solution, 80 ml of saturated salt water, and 150 ml of water in this order. The resultant organic layer was dehydrated with magnesium sulfate, and then filtered out. The solvent was removed by means of an evaporator, thereby there was obtained 5.67 grams of a target material represented with the general formula (IX) in the form of viscous liquid. The yield was 90%.

Elemental Analysis Value (Weight %) C: 68.9 (68.5) H: 8.9 (8.6)

The figures in parentheses indicate calculation values calculated with C$_{20}$H$_{30}$O$_5$ whose MW is 350.454.

IR(cm$^{-1}$): 2950, 2872 ($v_{CH}$), 1720 ($v_{C=O}$), 1630 ($v_{C=C}$), 1166 ($v_{C-O}$)

$^1$H-NMR (CDCl$_3$, internal standard material: tetramethylsilane) ppm: 1.0–2.7 (m, 14H), 1.2 (t, 3H), 1.45 (d, 3H), 1.95 (s, 3H), 3.75 (q, 2H), 3.8–4.1 (m, 2H), 5.55 (s, 1H), 5.9 (q, 1H), 6.1 (s, 1H)

[Embodiment 6]

Synthesis of vinylmonomer represented with the general formula (I) wherein R$^1$ indicates a methyl group, R$^2$ indicates a tricyclo[5.2.1.0$^{2,6}$]decane-4,8-diyl group, R$^3$ indicates a 1-butoxyethyl group, X indicates —CH$_2$—, and Y indicates a coupling group composed of carbon-carbon bonds.

(X)

In the same way as the embodiment 5, synthesis was carried out using butylvinylether in place of vinylethylether. The obtained target material represented with the general formula (X) was in the form of viscous liquid. The yield was 70%.

Elemental Analysis Value (Weight %) C: 69.5 (69.8) H: 8.7 (9.1)

The figures in parentheses indicate calculation values calculated with C$_{22}$H$_{34}$O$_5$ whose MW is 378.5076.

[Embodiment 7]

Synthesis of vinylmonomer represented with the general formula (I) wherein R$^1$ indicates a methyl group, R$^2$ indicates a tricyclo[5.2.1.0$^{2,6}$]decane-4,8-diyl group, R$^3$ indicates a tert-butyl group, X indicates —CH$_2$—, and Y indicates a coupling group composed of carbon-carbon bonds.

(XI)

Followings were put into 100 ml round bottom flask equipped with a calcium chloride (CaCl$_2$) tube:

(a) 5 grams (0.018 mol) of the vinylmonomer having been obtained in the embodiment 1;

(b) 30 ml of methylene chloride;

(c) 3.99 grams (0.054 mol) of t-butylalcohol; and (d) 1.76 grams (0.014 mol) of 4-dimethylaminopyridine.

The mixture was kept at 0° C. Into the mixture was gradually added 4.08 grams (0.020 ml) of dicyclohexylcarbodiimide. The mixture solution was stirred at 0° C. for five minutes, and then further stirred at room temperature for four hours. The precipitated cyclohexyl urea was filtered out, and then the filtrate was cleansed with 10 ml of 0.5M HCl and 10 ml of saturated sodium bicarbonate aqueous solution in this order. The cleansing was carried out twice each for HCl and sodium bicarbonate aqueous solution. The resultant organic layer was dehydrated with magnesium sulfate, and then filtered out. The solvent was removed by means of an evaporator, and then the resultant was refined with a silica gel column, thereby there was obtained 5.67 grams of a target material represented with the general formula (XI) in the form of viscous liquid. The yield was 90%.

Elemental Analysis Value (Weight %) C: 71.4 (71.8) H: 8.7 (9.0)

The figures in parentheses indicate calculation values calculated with $C_{20}H_{30}O_4$ whose MW is 334.4546.

IR(cm$^{-1}$): 2950, 2874 ($v_{CH}$), 1716 ($v_{C=O}$), 1626 ($v_{C=C}$), 1166 ($v_{C-O}$)

[Embodiment 8]

Synthesis of vinylmonomer represented with the general formula (I) wherein $R^1$ indicates a methyl group, $R^2$ indicates a norbornanediyl group, $R^3$ indicates a hydrogen atom, X indicates a coupling group composed of oxygen-carbon bonds, and Y indicates a coupling group composed of carbon-carbon bonds.

(XII)

Followings were put into 200 ml flask:

(a) 50 grams of bicyclo[2.2.1]hept-5-ene-2-carboxylic acid tert-butylester;

(b) 133 grams of methacrylic acid;

(c) 1.35 grams of conc. sulfuric acid; and (d) 2 grams of water.

The mixture was stood for reaction at the temperature in the range of 60° C. to 70° C. for 5 hours. After cooled down, methacrylic acid which had not reacted was removed under reduced pressure, and then the residue was refined by means of a silica gel column, thereby there Was obtained 2 grams of a target material represented with the general formula (XII) in the form of viscous liquid.

IR(cm$^{-1}$): 2400–3600 ($v_{OH}$), 2960, 2880 ($v_{CH}$), 1704 ($v_{C=O}$), 1628 ($v_{C=C}$), 1168 ($v_{C-O}$)

$^1$H-NMR (CDCl$_3$, internal standard material: tetramethylsilane) ppm: 1.25–2.05 (6H), 1.92 (3H), 2.3–2.85 (3H) 4.69–4.74 (1H), 5.53 (1H), 6.06 (1H)

[Embodiment 9]

Synthesis of polymer of the vinylmonomer having been obtained in the embodiment 1, represented with the general formula (II) wherein $R^4$ indicates a methyl group, $R^5$ indicates a tricyclo[5.2.1.0$^{2,6}$]decane-4,8-diyl group, A indicates —CH$_2$—, B indicates a coupling group composed of carbon-carbon bonds, and m=n=0.

(XIII)

In 50 ml flask having a reflux tube equipped with a calcium chloride (CaCl$_2$) tube, 1.58 grams (5.68 mmol) of the vinylmonomer having been obtained in the embodiment 1 was dissolved in 14 ml of dry tetrahydrofuran, and then 91.5 mg (40 mmol/liter) of azobisisobutyronitrile (hereinafter, referred to simply as AIBN), a polymerization initiator, was further added thereinto. Then, the mixture was stirred at the temperature in the range of 60° C. to 65° C. The mixture was stood for six hours, and then cooled down. Then, the resultant mixture was introduced into 300 ml of ligroin. The precipitated deposit was filtered out. Another reprecipitation refining was carried out, thereby there was obtained 0.767 grams of a target material represented with the general formula (XIII). The yield was 49%.

The molecular weight of the target material was measured using tetrahydrofuran as a solvent by means of the model GPC KF-803, a GPC column, commercially available from Showa Denko.

Molecular Weight: MW=6000, MW/MN=2.53 (polystyrene equivalent molecular weight)

IR(cm$^{-1}$): 2800–3600 ($v_{OH}$), 2950 ($v_{CH}$), 1722, 1696 ($v_{C=O}$), 1170 ($v_{C-O}$)

$^1$H-NMR ((CD$_3$)$_2$SO, internal standard material: tetramethylsilane) ppm: 0.7–2.8 (m, 19H), 3.4–4.0 (m, 2H), 11.8–42.1 (br s, 1H)

[Embodiment 10]

Synthesis of copolymer of the vinylmonomers having been obtained in the embodiments 1 and 3, which copolymer is represented with the general formula (II) wherein each of $R^6$ and $R^4$ indicates a methyl group, each of $R^5$ and $R^7$ indicates a tricyclo[5.2.1.0$^{2,6}$]decane-4,8-diyl group, $R^8$ indicates a tetradydropyran-2-yl group, each of A and D indicates —CH$_2$—, each of B and E indicates a coupling group composed of carbon-carbon bonds, and n=0.

(XIV)

In 100 ml flask having a reflux tube equipped with a calcium chloride (CaCl$_2$) tube, 2 grams (0.007 mmol) of the vinylmonomer having been obtained in the embodiment 1 and 10.42 grams (0.029 mol) of the vinylmonomer having been obtained in the embodiment 3 were dissolved in 50 ml of dry tetrahydrofuran, and then 163 mg (20 mmol/liter) of AIBN, a polymerization initiator, was further added thereinto. Then, the mixture was stirred at the temperature in the range of 60° C. to 65° C. The mixture was stood for six hours, and then cooled down. Then, the resultant mixture was introduced into 600 ml of ligroin. The precipitated deposit was filtered out. Another reprecipitation refining was carried out, thereby there was obtained 5.5 grams of a target material represented with the general formula (XIV). The yield was 59%. A copolymerization ratio in the above mentioned copolymerization was 2:8, calculating from an integration ratio of $^1$H-NMR (k=0.2, m=0.8).

Molecular Weight: MW=28000,

MW/MN=2.25 (polystyrene equivalent molecular weight)

[Embodiments 11 and 12]

In the same way as the embodiment 10, the vinylmonomer having been obtained in the embodiment 1 was polymerized with the vinylmonomer having been obtained in the embodiment 3 in a different mixture ratio from that of the embodiment 10. Copolymerization ratios (k/m) and weight average molecular weights (MW) of the obtained polymers are shown in Table 2.

TABLE 2

| | Mixture Ratio | k/m | Weight Average Molecular Weight (MW) |
|---|---|---|---|
| Embodiment 11 | 0.5/0.5 | 0.52/0.48 | 26000 |
| Embodiment 12 | 0.7/0.3 | 0.71/0.29 | 32000 |

[Embodiments 13 and 14]

In the same way as the embodiment 10, the vinylmonomer having been obtained in the embodiment 1 was polymerized with the vinylmonomer having been obtained in the embodiment 3 in a different amount or concentration of AIBN from that of the embodiment 10. A copolymerization ratio (k/m) and weight average molecular weights (MW) of the obtained polymers are shown in Table 3.

TABLE 3

| | AIBN Concentration | k/m | Weight Average Molecular Weight (MW) |
|---|---|---|---|
| Embodiment 13 | 10 mmol/liter | 0.22/0.78 | 76000 |
| Embodiment 14 | 40 mmol/liter | 0.21/0.79 | 6800 |

[Embodiment 15]

Synthesis of copolymer of the vinylmonomers having been obtained in the embodiments 1 and 7, which copolymer is represented with the general formula (II) wherein each of $R^4$ and $R^6$ indicates a methyl group, each of $R^5$ and $R^7$ indicates a tricyclo[5.2.1.0$^{2.6}$]decane-4,8-diyl group, $R^8$ indicates a tert-butyl group, each of A and D indicates —CH$_2$—, each of B and E indicates a coupling group composed of carbon-carbon bonds, and n=0.

In the same way as the embodiment 10, the vinylmonomer having been obtained in the embodiment 1 was polymerized with the vinylmonomer having been obtained in the embodiment 7 in place of the vinylmonomer of the embodiment 3 in a different mixture ratio from that of the embodiment 10. A copolymerization ratio (k/m) and weight average molecular weight (MW) of the obtained polymer, which is represented with the above general formula (XV), are shown in Table 4.

TABLE 4

| | Mixture Ratio | k/m | Weight Average Molecular Weight (MW) |
|---|---|---|---|
| Embodiment 15 | 0.6/0.4 | 0.58/0.42 | 28000 |

[Embodiment 16]

Synthesis of terpolymer of the vinylmonomer having been obtained in the embodiments 1 and 3 and tricyclo[5.2.1.0$^{2.6}$]decanylmethacrylate, which terpolymer is represented with the general formula (II) wherein each of $R^4$, $R^6$ and $R^9$ indicates a methyl group, $R^5$ and $R^7$ indicates a tricyclo[5.2.1.0$^{2.6}$]decane-4,8-diyl group, $R^8$ indicates a tetrahydropyran-2-yl group, each of A and D indicates —CH$_2$—, each of B and E indicates a coupling group composed of carbon-carbon bonds, and $R^{10}$ indicates a tricyclo[5.2.1.0$^{2.6}$]decanyl group.

In 200 ml flask having a reflux tube equipped with a calcium chloride (CaCl$_2$) tube, 1 gram (0.004 mmol) of the vinylmonomer having been obtained in the embodiment 1, 3.91 grams (0.011 mol) of the vinylmonomer having been obtained in the embodiment 3, and 4.75 grams (0.022 mol) of tricyclo[5.2.1.0$^{2.6}$]decanylmethacrylate commercially available from Hitachi Kasei K. K. in the article number FA-513M were dissolved in 75 ml of dry tetrahydrofuran, and then 5 mg (20 mmol/liter) of azobisisobutyronitrile (AIBN) was further added thereinto. Then, the mixture was stirred at the temperature in the range of 60° C. to 65° C. The mixture was stood for six hours, and then cooled down. Then, the resultant mixture was introduced into 600 ml of ligroin. The precipitated deposit was filtered out. Another reprecipitation refining was carried out, thereby there was obtained 6.8 grams of a target material represented with the general formula (XVI). The yield was 53%.

In the copolymerization, k=0.1, m=0.31 and n=0.59.

Molecular Weight: MW=32000

MW/MN=2.33 (polystyrene equivalent molecular weight)

[Embodiments 17 and 18]

In the same way as the embodiment 16, the vinylmonomer having been obtained in the embodiment 1 was polymerized with the vinylmonomer having been obtained in the embodiment 3 and tricyclo[5.2.1.0$^{2.6}$]decanylmethacrylate in a different mixture ratio from that of the embodiment 16. Copolymerization ratios (k/m/n) and weight average molecular weights (MW) of the obtained polymers are shown in Table 5.

TABLE 5

|  | Mixture Ratio | k/m/n | Weight Average Molecular Weight (MW) |
|---|---|---|---|
| Embodiment 17 | 0.2/0.4/0.4 | 0.21/0.40/0.39 | 24600 |
| Embodiment 18 | 0.5/0.2/0.3 | 0.50/0.22/0.28 | 25200 |

[Embodiment 19]

In the same way as the embodiment 17, polymerization was carried out with an amount or concentration of AIBN being 40 mmol/liter in place of 20 mmol/liter. Copolymerization ratios (k/m/n) and weight average molecular weights (MW) of the obtained polymers are shown in Table 6.

TABLE 6

|  | k/m/n | Weight Average Molecular Weight (MW) |
|---|---|---|
| Embodiment 19 | 0.21/0.41/0.38 | 6500 |

[Embodiment 20]

Synthesis of terpolymer of the vinylmonomer having been obtained in the embodiments 1 and 3 and isobornylmethacrylate, which terpolymer is represented with the general formula (II) wherein each of $R^4$, $R^6$ and $R^9$ indicates a methyl group, $R^5$ and $R^7$ indicates a tricyclo [5.2.1.0$^{2.6}$]decane-4,8-diyl group, $R^8$ indicates a tetrahydropyran-2-yl group, $R^{10}$ indicates an isobornyl group, each of A and D indicates —$CH_2$—, and each of B and E indicates a coupling group composed of carbon-carbon bonds.

(XVII)

In the same way as the embodiment 16, polymerization was carried out using isobornylmethacrylate, commercially available from Kyoei Kagaku K. K. under the trade name of Light Ester 1B-X, in place of tricyclo[5.2.1.0$^{2.6}$] decanylmethacrylate. A copolymerization ratio (k/m/n) and weight average molecular weight (MW) of the obtained polymer, which is represented with the general formula (XVII), are shown in Table 7.

TABLE 7

|  | Mixture Ratio | k/m/n | Weight Average Molecular Weight (MW) |
|---|---|---|---|
| Embodiment 20 | 0.1/0.3/0.6 | 0.12/0.31/0.57 | 24600 |

[Embodiment 21]

Synthesis of copolymer of the vinylmonomers having been obtained in the embodiments 8 and 7, which copolymer is represented with the general formula (II) wherein each of $R^4$ and $R^6$ indicates a methyl group, $R^5$ indicates a norbornanediyl group, $R^7$ indicates a tricyclo[5.2.1.0$^{2.6}$]decane-4, 8-diyl group, $R^8$ indicates a tert-butyl group, A indicates a coupling group composed of oxygen-carbon bonds, D indicates —$CH_2$—, each of B and E indicates a coupling group composed of carbon-carbon bonds, and n=0.

(XVIII)

In the same way as the embodiment 15, polymerization was carried out using the vinylmonomer having been obtained in the embodiment 8 in place of the vinylmonomer having been obtained in the embodiment 1. A copolymerization ratio (k/m) and weight average molecular weight (MW) of the obtained polymer, which is represented with the above general formula (XVIII), are shown in Table 8.

TABLE 4

|  | Mixture Ratio | k/m | Weight Average Molecular Weight (MW) |
|---|---|---|---|
| Embodiment 21 | 0.6/0.4 | 0.59/0.41 | 26300 |

[Embodiment 22]

There was prepared a resist composed of the following materials A, B and C. The experiment mentioned hereinbelow was carried out under a yellow lamp.

A. 0.970 grams of the resin having been synthesized in the embodiment 11

B. 0.030 grams of cyclohexylmethyl(2-oxocyclohexyl) sulfoniumtrifluoromethanesulfonate This is a photo acid generator represented with the general formula (III).

C. 4.000 grams of propyleneglycolmonomethylether acetate

This is a solvent.

Figure 1:
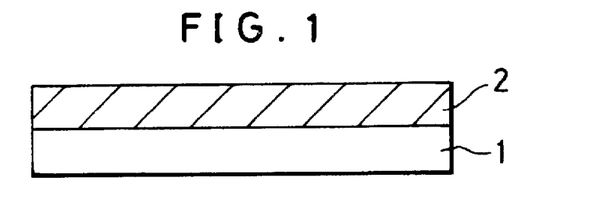
FIGS. 1 to 3 are a cross-sectional views of a wafer for showing steps of a method of forming a positive pattern on the wafer by using a photoresist in accordance with the invention.

The mixture composed of the above mentioned materials A, B and C was filtrated with 0.2 μm teflon filter to thereby prepare a resist. On a quartz substrate 3 inches thick was applied the thus prepared resist by spin coating process, and then the resist was baked at 90 degrees centigrade for 60 seconds on a hot plate. Thus, on the substrate 1 was formed a thin layer 2 having a thickness of 1.0 μm, as illustrated in FIG. 1. The dependency of a transmissivity of the thin layer 2 on a wavelength was measured by use of a spectrophotometer for ultraviolet and visible region. The transmissivity of the thin layer 2 at 193.4 nm was 65%. Thus, it was confirmed that the thin layer 2 had a sufficient transparency as a single layer resist.

[Embodiment 23]

In the same way as the embodiment 22, synthesis was carried out using the resin in accordance with the embodiment 17 in place of the resin in accordance with the embodiment 11. The obtained thin layer had the transmissivity of 67% at 193.4 nm, and hence it was confirmed that the thin layer had a sufficient transparency as a single layer resist.

[Embodiment 24]

In the same way as the embodiment 22, synthesis was carried out using the resin in accordance with the embodiment 22 in place of the resin in accordance with the embodiment 11, and also using 2-oxocyclohexylmethyl (2-norbornyl) sulfoniumtrifluoromethanesulfonate in place of cyclohexylmethyl(2-oxocyclohexyl) sulfoniumtrifluoromethanesulfonate. The obtained thin layer had the transmissivity of 68% at 193.4 nm, and hence it was confirmed that the thin layer had a sufficient transparency as a single layer resist.

[Embodiment 25]

Into 10 grams of diethyleneglycoldimethylether was dissolved 2 grams of the resin having been obtained in the embodiment 11, and the thus prepared solution was filtrated through a 0.2 μm teflon filter. On a silicon substrate 3 inches thick was applied the thus prepared resist by spin coating process, and then the resist was baked at 90 degrees centigrade for 60 seconds on a hot plate. Thus, there was formed a thin layer having a thickness of 0.7 μm. The etching rate of the thus obtained thin layer against $CF_4$ gas was measured by means of a reactive ion etching (RIE) apparatus, commercially available from Nichiden Aneruva at the model number DEM 451, under etching conditions as follows: Power=100 W, Pressure=5 Pa and Gas Flow Rate=30 sccm. The results obtained were shown in Table 9.

In the same way, the etching rates were measured for the resins having been obtained in the embodiments 15 and 17. In comparison, the measured etching rate of polymethylmethacrylate which is a resin having no bridged cyclic hydrocarbon groups in a molecular structure.

TABLE 9

|  | Etching Rate (Å/min) |
|---|---|
| Resin of Embodiment 11 | 212 |
| Resin of Embodiment 15 | 209 |
| Resin of Embodiment 17 | 198 |
| Polymethylmethacrylate | 330 |

The results shown in Table 9 confirmed that the resin used in the present invention had slow etching rate against $CF_4$ gas, and hence had superior dry-etch resistance.

[Embodiment 26]

Figure 2:
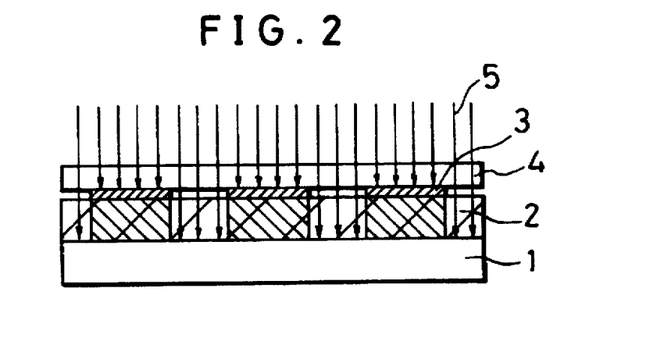
Figure 3:
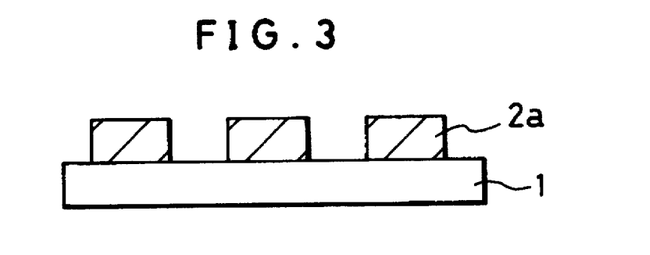
Figure 4:
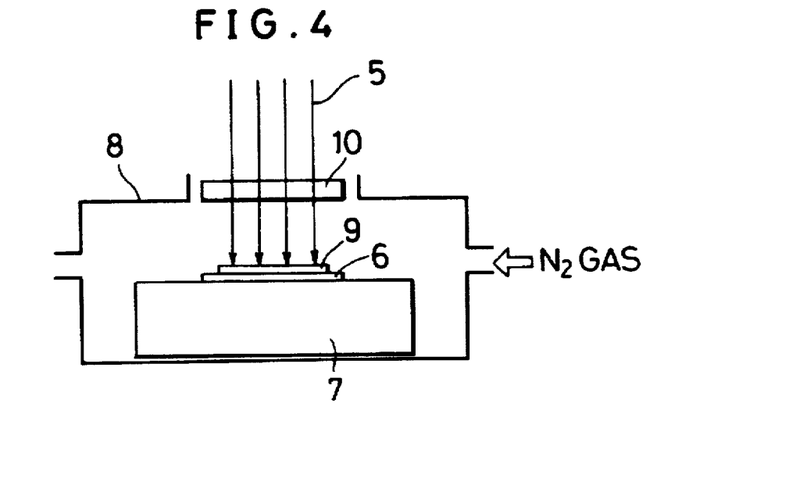
FIG. 4 is a schematic view illustrating an experimental device for exposing a wafer to a light.

As illustrated in FIG. 4, a wafer 6 having a film composed of the resist shown in the embodiment 22 was placed on an X-Y stage 7 in an exposure apparatus 8 sufficiently purged with nitrogen. On the resist layer was closely placed a mask 9 comprising a quartz plate 4 on which a pattern 3 composed of chrome is formed, and then ArF excimer laser beam 5 was irradiated to the resist layer through a homogenizer 10 and further through the mask 9, as illustrated in FIG. 2. Shortly after that, the wafer 6 was baked on a hot plate at 90 degrees centigrade for 60 seconds, and then was developed by dipping in an alkaline developing reagent for 60 seconds. The alkaline developing reagent contained tetramethylammoniumhydroxide at 2.3 weight part and was maintained at 23 degrees centigrade. Subsequently, the wafer 6 was rinsed in pure water for 60 seconds. As a result, only exposed regions of the resist layer was dissolved and thus removed in the developing reagent, thereby there was obtained a positive type pattern 2a, as illustrated in FIG. 3. In this experiment, a resolution of 0.25 μm line and space (L/S) was obtained when the exposure energy was approximately 35 mJ/cm². The resolved pattern was also observed with a scanning electron microscope (SEM) commercially available from Hitachi Co. Ltd., under the tradename of SE-4100 with the result that undeveloped regions and peel-off of the pattern were not observed.

[Embodiment 27]

In the same way as the embodiment 26, a pattern resolution experiment was carried out using the resist shown in the embodiment 23 in place of the resist shown in the embodiment 22. The result of the experiment was that a resolution of 0.25 μm line and space was obtained when the exposure energy was 35 mJ/cm².

[Embodiment 28]

In the same way as the embodiment 26, a pattern resolution experiment was carried out using the resist shown in the embodiment 24 in place of the resist shown in the embodiment 22. The result of the experiment was that a resolution of 0.25 μm line and space was obtained when the exposure energy was 28 mJ/cm².

As having been explained so far in connection with the preferred embodiments, the photoresist in accordance with the present invention has (a) high transparency to far ultraviolet (FUV) radiation region having a wavelength of 220 nm or shorter, (b) high sensitivity and resolution to FUV exposure light, and (c) enhanced dry-etch resistance. Thus, the photoresist in accordance with the present invention is suitable for far ultraviolet radiation having a wavelength of 220 nm or shorter as exposure light, and is suitable for in particular ArF excimer laser. In addition, the photoresist in accordance with the invention makes it possible to form a minute pattern necessary for manufacturing a semiconductor element.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A vinylmonomer represented with the following general formula (I):

wherein $R^1$ represents one of a hydrogen atom and a methyl group, $R^2$ represents a dihydric, bridged cyclic hydrocarbon group having a carbon number in the range of 7 to 13 both inclusive, $R^3$ represents one of a hydrogen atom and an acid decomposable group, X represents one of an alkylene group and a coupler for coupling elements with each other so that an oxygen-carbon bond is established between said elements, and Y represents one of an alkylene group and a coupler for coupling elements with each other so that a carbon-carbon bond is established between said elements.

2. The vinylmonomer as set forth in claim 1, wherein said dihydric, bridged cyclic hydrocarbon group represented with $R^2$ is selected from the group consisting of a tricyclo [5.2.1.0$^{2,6}$] decanediyl group, an adamantanediyl group, a norbornanediyl group, a methylnorbornanediyl group, an isobornanediyl group, tetracyclo [4.4.0.1$^{2,5}$.1$^{7,10}$] dodecanediyl group, and a methyltetracyclo [4.4.0.1$^{2,5}$.1$^{7,10}$] dodecane-diyl group.

3. The vinylmonomer as set forth in claim 1, wherein said group represented with $R^3$ is selected from a group consisting of a tert-butyl group, a tetrahydropyran-2-yl group, a tetrahydrofuran-2-yl group, a 4-methoxytetrahydrofuran-4-yl group, a 1-ethoxyethyl group, a 1-butoxyethyl group, a 1-propoxyethyl group, and a 3-oxocyclohexyl group.

* * * * *